United States Patent
Müller et al.

(10) Patent No.: US 6,183,719 B1
(45) Date of Patent: *Feb. 6, 2001

(54) HIGH SURFACE AREA ALUMINA SOLID

(75) Inventors: Ulrich Müller, Neustadt; Roger Ruetz, Mannheim, both of (DE)

(73) Assignee: BASF Aktiengesellschaft, Ludwigshafen (DE)

( * ) Notice: Under 35 U.S.C. 154(b), the term of this patent shall be extended for 0 days.

This patent is subject to a terminal disclaimer.

(21) Appl. No.: 09/245,729

(22) Filed: Feb. 8, 1999

Related U.S. Application Data

(63) Continuation of application No. 09/114,202, filed on Jul. 13, 1998, now Pat. No. 5,911,966.

(30) Foreign Application Priority Data

Jul. 14, 1997 (DE) .............................. 197 30 126

(51) Int. Cl.[7] ...................................... C01F 7/02
(52) U.S. Cl. ........................ 423/625; 502/314; 502/320; 502/322; 502/323; 502/327; 502/332; 502/341; 502/415; 554/76

(58) Field of Search ..................... 502/314, 320, 502/322, 323, 327, 332, 341, 415; 423/625; 554/76

(56) References Cited

U.S. PATENT DOCUMENTS

| | | | | |
|---|---|---|---|---|
| 3,908,002 | * | 9/1975 | Holler | 423/628 |
| 4,179,408 | * | 12/1979 | Sanchez et al. | 252/448 |
| 4,216,122 | * | 8/1980 | Michalko | 252/448 |
| 4,279,779 | * | 7/1981 | Sanchez et al. | 252/448 |
| 4,371,513 | * | 2/1983 | Sanchez et al. | 423/625 |
| 4,390,456 | * | 6/1983 | Sanchez et al. | 252/448 |
| 4,649,037 | * | 3/1987 | Marsh et al. | 423/338 |
| 4,835,124 | * | 5/1989 | Pearson | 501/127 |
| 5,354,548 | * | 10/1994 | Araya et al. | 423/700 |
| 5,445,807 | * | 8/1995 | Pearson | 423/625 |

* cited by examiner

Primary Examiner—Tom Dunn
Assistant Examiner—Cam N. Nguyen
(74) Attorney, Agent, or Firm—Keil & Weinkauf

(57) ABSTRACT

An alumina solid is obtainable by a process comprising the step of contacting in a liquid medium at least one alumina precursor with at least one template comprising a membrane lipid or a mixture of two or more thereof.

6 Claims, 3 Drawing Sheets

HIGH SURFACE AREA ALUMINA SOLID

Continuation of application Ser. No. 09/114,202, filed Jul. 13, 1998, U.S. Pat. No. 5,911,966.

The present invention relates to a high specific surface area alumina solid, to a process for preparing it and to the use of membrane lipids as templates.

The preparation of alumina solids is known per se. A survey of the processes currently in industrial use is given in Ullmann's Encycl. Tech. Chem. 5th Ed. 1997, pp. 561–562, and in Winnacker, Küchler, 4th edition, Hanser-Verl. 1983 vol. 3, pp. 2–41.

Alumina thus prepared has a specific surface area in the range from 100 to 400 $m^2/g$ and pore diameters of from 2 to 5 nm, with large-pore aluminas generally having smaller surface areas. Such large-pore aluminas have a broad pore size distribution up to 10 nm.

Mesoporous oxides have likewise been described, for example in DE-A 44 07 326 and DE-A 195 43 638. According to these references, mesoporous oxides are prepared by adding a cationic, anionic or nonionic surfactant as a structure-directing reagent, or template, to the oxide precursors (monomers or oligomers) in the course of the polycondensation process to give an inorganic oxide. According to these references, the actual synthesis is followed by thermal removal of the template surfactants, for example by calcining in air at from 350 to 600° C., giving rise to a mesoporous, purely inorganic oxide.

"Mesoporous" means that the diameter of the pores in the solid is from about 2 to about 50 nm.

The pores of prior art mesoporous oxides are predominantly confined to the range around 2 nm or so.

However, oxide solids which have larger pores and which are inexpensive to produce are desirable for some applications, for example for use as heterogeneous catalysts, to optimize mass transfer in the reaction. This aim is achieved with some of the commercially available aluminas which, however, have broad pore diameter distributions and small specific surface areas. Furthermore, heat treatment may lead to the formation of various crystalline alumina phases (eg. $\gamma$-$Al_2O_3$ or, at even higher temperatures, $\gamma$-$Al_2O_3$) some of which have inherent catalytic properties such as Lewis or Bronsted acidity and therefore have an undesirable effect on the reaction to be catalyzed.

It is an object of the present invention to provide an alumina solid which is suitable for a multiplicity of applications, in particular for use as catalyst or catalyst support, and a process for preparing this solid in an economically favorable, ie. inexpensive, way.

We have found that, surprisingly, this object is achieved by using a membrane lipid as template in the preparation of the alumina solid.

The present invention accordingly provides a process for preparing an alumina solid, which comprises the step of contacting in a liquid medium at least one alumina precursor with at least one template comprising a membrane lipid or a mixture of two or more thereof.

This invention further provides an alumina solid obtainable by a process comprising the step of contacting in a liquid medium at least one alumina precursor with at least one template comprising a membrane lipid or a mixture of two or more thereof.

Figure 1:
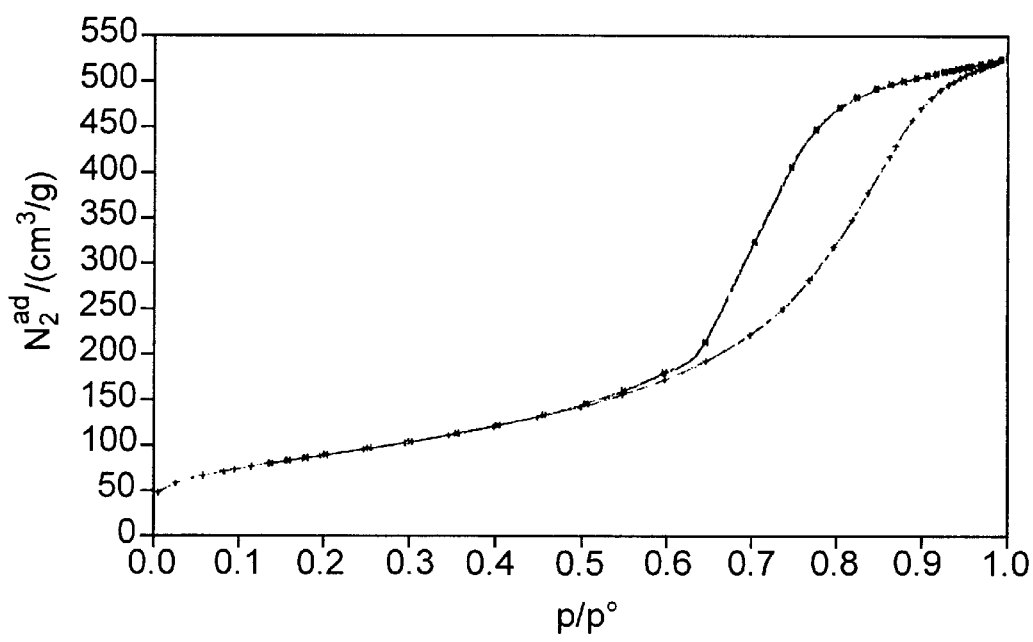
FIG. 1 shows the result of nitrogen adsorption on the solid of Example 1. Here, $p/p^0$ stands for the relative pressure, $N_2^{ad}$ for nitrogen, adsorbed at the solid, + for measured values obtained during adsorption, and ++ for measured values obtained during desorption.

"Template" refers to a substance which is initially mixed with the starting materials and subsequently removed from the resulting solid, eg. by thermal treatment, to leave the areas of the solid in which the template was located in the form of pores.

As stated above, templates used according to the invention are membrane lipids such as phospholipids, glycolipids and cholesterol. The term "membrane lipid" as used herein is defined as in L. Stryer—Biochemie, Spektrum der Wissenschaft Verlagsgesellschaft mbH, 1990, p. 296 and refers to relatively small molecules which have a hydrophilic and a hydrophobic moiety and spontaneously form closed bimolecular layers in aqueous media. Such membrane lipids are described in detail in the abovementioned biochemistry textbook by L. Stryer on pp. 296ff. Furthermore, phospholipids in particular are described in Römpp-Chemielexikon, 9th ed., vol. 4, pp. 3383/3384, ThiemeVerlag 1991, and in an article by Eibl in Angew. Chem. 96 (1984), p. 247–262, which are all fully incorporated herein by reference for the membrane lipids and phospholipids.

Examples of preferred membrane lipids are sphingolipids, ie. phospholipids derived from sphingosine, phosphoglycerides, ie. phospholipids derived from glycerol, eg. phosphatidate, phosphatidyl serine, phosphatidyl ethanolamine, phosphatidyl choline, phosphatidyl inositol, diphosphatidyl glycerol, glycolipids, eg. cerebroside and cholesterol.

However, phospholipids are preferred templates.

It is of course also possible to use as templates mixtures of two or more membrane lipids, preferably mixtures of two or more of the membrane lipids cited above.

The amount of membrane lipid used is generally not subject to any particular restrictions and is preferably from about 0.05 to about 50% by weight, more preferably from about 2 to about 10% by weight, in each case based on the synthesis batch, ie. the total amount of alumina precursor, template and liquid medium.

Liquid media used in the process of the invention are preferably aqueous solutions, for example mixtures of water and alcohols, eg. ethanol and/or isopropanol. Contacting may also be carried out in water, an organic solvent or a mixture of different organic solvents.

Preference is given to using alcohol solvents generated by hydrolysis of the alumina precursors, ie., for example, ethanol when using aluminum ethoxide ($Al(OEt)_3$), isopropanol when using aluminum isopropoxide and butanol when using aluminum butoxide.

A usable alumina precursor is any compound which is converted to alumina by calcining in air at elevated temperatures. The precursor may be employed, for example, as an organometallic component, eg. as alkoxide, Grignard compound, alkylate, chelate, eg. with acetylacetonate, in a form which is soluble in an organic solvent, or in the form of soluble salts, as a hydroxide, as a colloid in an aqueous phase or as a combination of two or more thereof.

Contacting can be carried out at a basic, acidic or also at a neutral pH, preference being given to an acidic pH, especially a pH of from 1 to 5.

After combining the alumina precursor and the template in a liquid medium, the resulting suspension is brought to the appropriate pH and stirred at preferably from about –10 to 150° C., more preferably from about 10 to about 90° C., especially from about 20 to about 65° C., for about 0.5 to about 72 hours, preferably from about 1 to about 48 hours, especially from about 10 to about 30 hours. When contacting the components described above, the pressure is preferably from about 0.4 to about 300 bar, more preferably from about 0.8 to about 150 bar and especially from about 1 to about 10 bar.

The resulting suspension is then separated from the liquid medium, for example by centrifugation or simple filtration, and subsequently dried. Drying is preferably effected initially at ambient temperature for from about 5 to about 72 hours, preferably from about 10 to about 48 hours, especially from about 20 to about 30 hours, and then at an elevated temperature in the range of from about 50 to about 100° C., preferably from about 55 to about 70° C., for several hours.

The alumina solid dried in this manner is subsequently calcined at from about 350 to about 800° C., preferably from about 400 to about 700° C., especially from about 450 to about 600° C, for from about 2 to about 10 hours, preferably from about 4 to about 6 hours, in the presence of oxygen, preferably in air.

During the contacting of the alumina precursor with the template, the following additional components may be added:

pharmacologically active organic or inorganic compounds such as analgesics or cardiovascular agents, in which case the incorporation of these compounds into the alumina solid results in retarded release of the pharmacologically active compound on application;

enzymes for biotechnological application such as oxidases, reductases, transferases, hydrolases, lyases, isomerases, ligases and semi-synthetic and synthetic enzymes as described, for example, in Science, 223 (1984) p. 165ff, Cold Spring Harbor Symp. Quant.Biol. 52 (1987), I. 75–81, and Tetrahedron 40 (1994), p. 269–292, the relevant contents of which are fully incorporated herein by reference;

pigments such as ferromagnetic pigments, eg. chromium (IV) dioxide, ferrites, iron oxides, iron or iron alloys, further inorganic pigments, eg. chalk, graphite, titanium white, white lead or zinc white, carbon black, luminescent pigments, eg. zinc sulfide or alkaline earth metal aluminates, organic pigments such as azo pigments, indigoid pigments, phthalocyanine pigments, metal complex pigments or diketopyrrolopyrrole pigments, which are likewise present in encapsulated form in the resulting alumina solid.

In the preparation of the alumina solid of the invention, it is also possible to add, in particular via the aqueous phase, an ionic compound of an element of main groups I to III except aluminum or of transition groups I to VIII of the Periodic Table of the Elements, the lanthanoids, silicon, germanium, tin, lead, phosphorus, antimony, bismuth, sulfur, selenium, tellurium or a mixture of two or more thereof, preferably sodium, potassium, calcium, magnesium, beryllium, boron, gallium, indium, silicon, germanium, tin, lead, antimony, bismuth, scandium, yttrium, lanthanum, titanium, zirconium, hafnium, vanadium, niobium, tantalum, chromium, molybdenum, tungsten, manganese, rhenium, iron, cobalt, nickel, ruthenium, copper, zinc, cadmium, mercury, cerium, europium, thorium, uranium or a mixture of two or more thereof, more preferably sodium, potassium, calcium, magnesium, beryllium, boron, gallium, indium, silicon, germanium, tin, lead, bismuth, titanium, zirconium, hafnium, vanadium, niobium, tantalum, chromium, molybdenum, tungsten, manganese, rhenium, iron, cobalt, nickel, ruthenium, copper, zinc, cadmium, mercury, cerium or a mixture of two or more thereof.

The elements cited above may be employed especially in the form of their sulfates, phosphates, nitrates, carbonates, halides and perchlorates and also in the form of easily hydrolyzable organometallic compounds such as alcoholates, chelates, carboxylates, preferably in the form of sulfates, phosphates and nitrates, more preferably in the form of sulfates and nitrates.

They can also be employed in the form of isopoly cations or heteropoly cations as described in references DE-A 44 07 326 and DE-A 195 43 638 which were mentioned at the beginning and the relevant contents of which are likewise fully incorporated herein by reference.

In a further embodiment of the present invention, the mixture of alumina precursor, template and liquid medium may be applied to an inert porous support, for example a porous glass, a silica gel, diatomaceous earth or clay, a ceramic material, a metal, a metal packing or a metal mesh as used for static mixers or reactive distillation column packings, for example. This makes it possible to produce inert supports covered or impregnated with alumina solid by the process of the invention to provide composite materials which have improved mechanical stability and improved permeability in the catalytic reactor compared to the starting materials.

In this context, metallic support materials, for example the stainless steels having the material numbers 1.4767, 1.4401, 2.4610, 1.4765, 1.4847, 1.4301, etc., are particulary useful since their surface can be roughened by heat treatment before they are covered/impregnated with the solids. Particular preference is given to using Kantahl (material number 1.4767) or alumina-containing metals as mesh material. Kantahl is an alloy containing about 75% by weight of Fe, about 20% by weight of Cr and about 5% by weight of Al. Heat treatment is effected by heating the metallic supports cited above in air at temperatures of from 600 to 1100° C., preferably from 800 to 1000° C., for from one to twenty hours, preferably from one to ten hours, and cooling back down. This pretreatment is described in EP-A-0 564 830 and important since the heat treatment significantly improves the bonding between the solids and the metallic supports.

If contacting is effected at a stationary interface, ie. at the interface of two immiscible fluids, the alumina solid may be obtained in the form of thin films or layers since the presence of such an interface makes it possible to provide the solid, during its preparation, with a particular oriented structure such as a thin film. Further details are described in DE-A 19624862.0. Thin films or layers obtained in this manner may be employed in membrane, separation or purification processes or may be used for information storage. Such applications are described, for example, in DE-A 44 24 221, the relevant contents of which are fully incorporated herein by reference.

Such solids may be utilized in particular for electronic, optical or electro-optic applications; corresponding membranes are utilized in the catalytic conversion in membrane reactors or in reactive distillations. The present invention accordingly also provides for the use of a solid of the invention as catalyst or catalyst support, as matrix for active components, in membrane, separation or purification processes, for producing electrical, optical or electro-optic components such as switching devices or sensors, for producing oxide ceramics or for separating substances, as adsorbent, as filler, especially in polymers, as fire retardant and as abrasives and polishing materials.

If the solid of the invention is used as catalyst or catalyst support, it is particularly useful in hydrocarbon oxyfunctionalization, olefin oxidation to give oxiranes, aromatics alkylation, hydrogenation, dehydrogenation, hydration, dehydration, isomerization, an addition reaction, an elimination reaction, nucleophilic or electrophilic substitution, dehydrocyclization, hydroxylation of heteroaromatic compounds, aromatics hydroxylation, epoxyaldehyde rearrangement, amination of monomeric or oligomeric olefins, an aldol type condensation reaction, a polymerization reaction, an esterification or etherification, the catalytic conversion of exhaust gases and flue gases and for nitrogen oxide removal.

The solid of the invention is in particular characterized by the following properties:

In X-ray analysis, its strongest reflections are in the angular range of less than 4°(2 η) when measured using Cu $K_\alpha$ radiation.

The solid has pores in the range from about 2 to about 50 nm, preferably from about 4 to about 30 nm, especially from about 6 to about 10 nm, the pore diameter being determined by nitrogen adsorption at 77 K. The specific surface area determined under the same conditions as evaluated by the method of Barret, Joyner and Halenda according to J. Am. Chem. Soc., 73 (1951), 373–380, is more than about 100 $m^2/g$, preferably more than about 250 $m^2/g$, especially from about 300 to 550 $m^2/g$. The pore volume, likewise determined by nitrogen adsorption at 77 K, is more than about 0.2 ml/g, preferably more than about 0.25 ml/g, especially from about 0.5 ml/g to 1.0 ml/g.

The present invention further provides the use of a membrane lipid or a mixture of two or more thereof as templates in the preparation of an alumina solid.

The Examples which follow illustrate the preparation and the properties of the solid of the invention and relate it to a Comparative Example prepared according to a prior art method, ie. without adding a membrane lipid.

EXAMPLES

Example 1

A solution of 205.8 g of aluminum triisopropoxide (Merck), 300 g of ethanol and 81.0 g isopropanol was homogenized for 30 minutes in a 2 l four-neck flask. 50.0 g of soybean lecithin PC 40–45 comprising 40–45% phosphatidyl choline, 10% phosphatidyl ethanolamine and 2% phosphatidyl inositol (Gienow, Pinneberg) were then added to this mixture. Upon addition of a solution of 650.0 g of deionized water and 7.5 g of hydrochloric acid solution (10% by weight) a suspension was formed. The suspension was stirred at room temperature for 24 h, filtered and dried in air for 24 h. The solid was then dried at 60° C. overnight. 124 g of solid were obtained. The solid was finally calcined in air at 500° C. for 5 hours. The loss on calcination was 113% by weight, based on the solid used.

Nitrogen adsorption at 77 K gave a typical hysteresis in the relative pressure range $p/p^0$>0.6 as shown in FIG. 1. Application of the BJH model to these results gave a pore surface area of 497 $m^2/g$ for pores in the range from 6 to 7 nm. The corresponding pore volume was 0.81 ml/g as determined at a relative pressure $p/p^0$ of 0.98. The most frequent pore diameter was about 7 nm.

Figure 2:
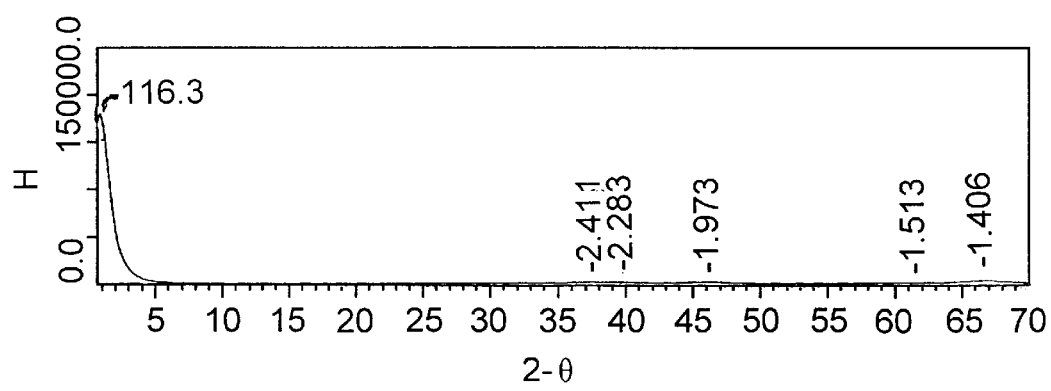
FIG. 2 shows the X-ray diffraction pattern of the solid of Example 1. Here, I stands for the intensity of the registered signal in count units.
Figure 2A:
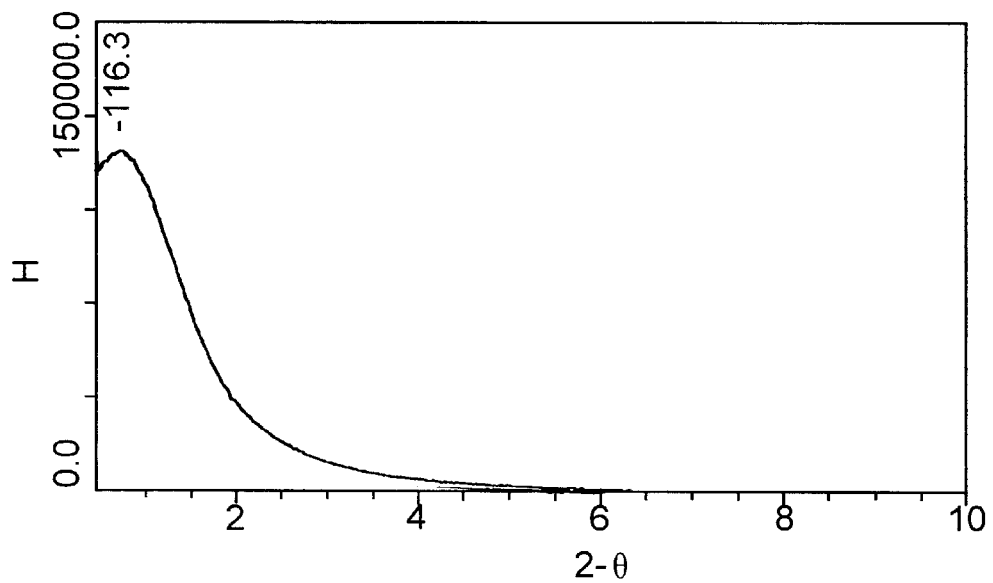
FIGS. 2a and 2b show enlargements of details of this X-ray diffraction pattern.
Figure 2B:
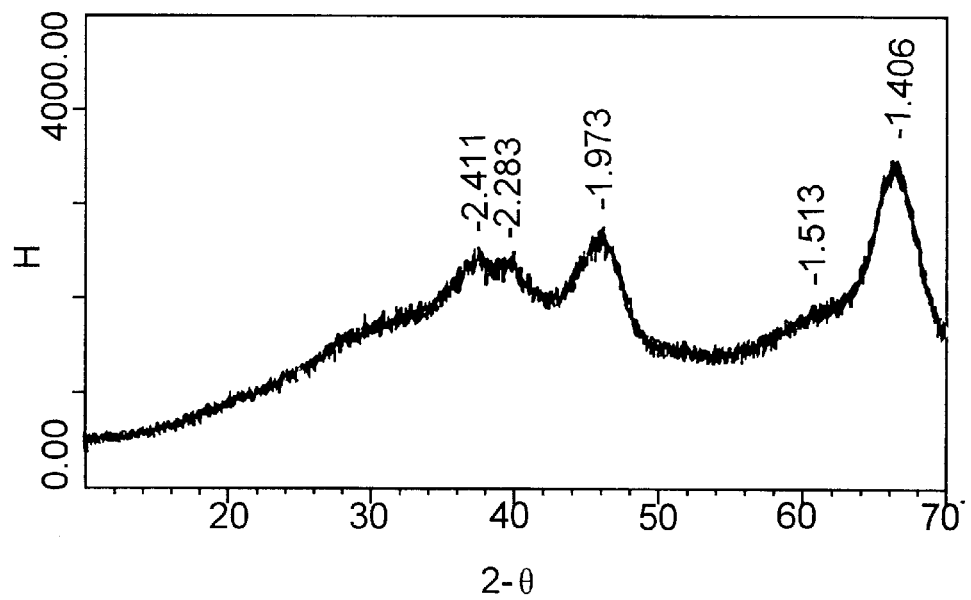

X-ray analysis of the solid obtained in this manner gave the highest reflection intensities at angles of less than 4° (2θ) (Cu $K_\alpha$ radiation). The diffraction pattern is shown in FIGS. 2, 2a and 2b.

Comparative Example 1

A solution of 205.8 g of aluminum triisopropoxide (Merck), 300 g of ethanol and 51.0 g of isopropanol was homogenized for 30 minutes in a 2 l four-neck flask. Upon addition of a solution of 650.0 g of water and 7.5 g of the hydrochloric acid solution (10% by weight) a white suspension was formed. The white suspension was stirred at room temperature for 24 h, filtered and dried at room temperature in air for 24 h and then at 60° C. overnight. 87.7 g of solid were obtained. The solid was finally calcined at 500° C. for 5 hours. The loss on calcination was 28.2% by weight.

X-ray analysis of the solid obtained in this manner gave no distinct reflections at angles of less than 4° (2 θ). The solid was pure γ-$Al_2O_3$.

Nitrogen adsorption at 77 K gave typical hysteresis in the relative pressure range $p/p^0$>0.4. Application of the BJH model to these results gave pore sizes in the range from 2 to 5 nm. The pore surface area according to the BET method was 289 $m^2/g$. The corresponding pore volume was only 0.37 ml/g as determined at a relative pressure $p/p^0$ of 0.98. The most frequent pore diameter was about 3.8 nm.

We claim:

1. A process for preparing a porous alumina solid, which comprises the step of contacting in a liquid medium at least one alumina precursor with at least one template comprising a membrane lipid or a mixture of two or more thereof.

2. A process as claimed in claim 1, wherein the membrane lipid is a phospholipid or a mixture of two or more thereof.

3. A process as claimed in claim 1, wherein the alumina solid comprises at least one element selected from the group consisting of sodium, potassium, calcium, magnesium, beryllium, boron, gallium, indium, silicon, germanium, tin, lead, bismuth, titanium, zirconium, hafnium, vanadium, niobium, tantalum, chromium, molybdenum, tungsten, manganese, rhenium, iron, cobalt, nickel, ruthenium, copper, zinc, cadmium, mercury and cerium.

4. A process as claimed in claim 1, wherein the precursor is additionally contacted with a pharmacologically active organic or inorganic compound, an enzyme, a pigment or a mixture of two or more thereof.

5. A process as claimed in claim 1, wherein the contacting is carried out in the presence of an inert porous support or at a stationary interface.

6. A porous alumina solid obtained by a process comprising the step of contacting in a liquid medium at least one alumina precursor with at least one template comprising a membrane lipid or a mixture of two or more thereof, said process further comprising the step of calcining the alumina solid at temperatures of from about 350 to about 800° C., and said porous alumina solid has its strongest reflections, in X-ray analysis, in the angular range of less than 4° (2θ) when measured using Cu $K_\alpha$ radiation.

* * * * *